April 16, 1957 W. J. McKEE Plant Pat. 1,592
IRIS PLANT
Filed April 24, 1956
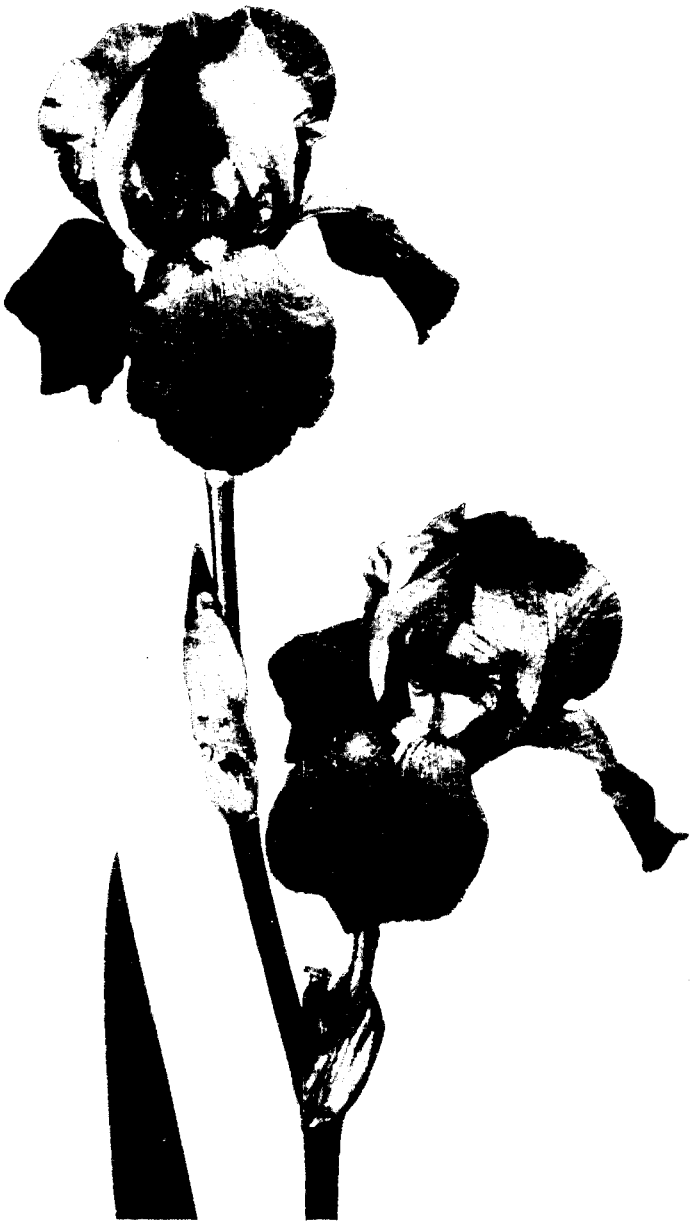
INVENTOR
William J. McKee
By Orville M. Kile
Plant Patent Agt.

United States Patent Office

Plant Pat. 1,592

Patented Apr. 16, 1957

1,592

IRIS PLANT

William J. McKee, Worcester, Mass., assignor to Schreiner's Gardens, Salem, Oreg.

Application April 24, 1956, Serial No. 580,421

1 Claim. (Cl. 47—60)

My new invention relates to a new and distinct variety of iris plant which originated from a cross of the variety Pequot (unpatented) and an unnamed seedling which in turn was a cross between Pequot and Hywill (both unpatented). The crosses were made by me at my home in Worcester, Massachusetts.

I have asexually reproduced this new variety by diversion of rhizomes, at my Worcester location, and the variety has since been similarly reproduced at Salem, Oregon.

Outstanding features of my new variety are that it produces very large flowers in great quantity, grows to a greater height and produces a truer red flower than any other known iris.

The accompanying illustration shows in approximately true colors, a portion of a stem of my new variety, with a bud and two open flowers; also a portion of the tip of a foliage blade.

In the following detailed description, color plate references indicate Ridgway's Color Standards and Nomenclature, while other color names refer to the ordinary dictionary meaning of the term.

*The plant*

Growth habit: Vigorous; stems plentifully branched; foliage grows in mound form and averages 28 inches in height, which is unusually tall for red iris varieties.

Propagation: Variety propagates easily by division of rhizomes, and at a good rate of reproduction.

Blooming habit: Blooms early-midseason. Usually floriferous and long-lasting. Each stem (with its side branches) may bear 11 or 12 buds and blossoms. An individual blossom last about three days and with 11 or 12 buds and blossoms on each stem, it is possible for a single stem to remain in bloom for 2 to 2½ weeks.

Disease resistance: Foliage is more free of disease than that of most other red iris varieties. This new variety has proved to be more resistant to leafspot than the variety Redwyne when grown under identical conditions at my nursery at Worcester, Massachusetts. While I have not grown this new variety under identical conditions with red varieties other than Redwyne, under similar conditions of growth it appears to be more free of leafspot than are other known red varieties.

Stems: Deep green, approximately Dark Dull Yellow Green (Plate XXXII). Strong and straight, rising upright to about 38 inches, which is greater than the height of most iris varieties and higher than any known red variety. Much branched, with side branches ranging from 14 inches in length on lower part of stem to 6 to 8 inches on upper part of stem.

Foliage:

*Height.*—Rising in mound form, the foliage averages approximately 28 inches in height.

*Color.*—Medium green, approximately Yew Green (Plate XXXI), rather than the bluish-green of most iris foliage. Retention of foliage color is extra good throughout the growing season until late fall.

*The flower*

Bud:

*Size.*—Approximately 1 to 1¼ inches long when color first shows, expanding rapidly so that the day before emergence into flower, buds are from 3 to 4 inches in length.

*Opening.*—Bud grows imperceptibly for several days then expands rapidly after color begins to show.

*Color.*—Brownish-red at tip. Enclosure (spathe) is light green, the papery portion being marked and overlaid with Corinthian Red (Plate XXVII) to Pecan Brown (Plate XXVII), the whole being edged with Corinthian Red.

Flower:

*Size.*—Large, measuring approximately 5½ inches from top to bottom, and about the same from side to side.

*Form.*—Classical; spherical; upper petals are cupped and firmly held in place. The three upper petals barely touch each other—in a graceful arch. Lower petals gracefully flare.

*Substance.*—Very good, withstanding all elements equally well, whether extremes of hot weather or the buffeting of wind and rain. Substance is held for the entire life of the bloom.

*Aspect.*—Shines like silk cloth, with a sparkling sheen greater than that of any other known red variety; also appears to have a plushy depth. There is no trace of distracting venation on the haft—a rare characteristic for a red iris.

*Keeping qualities.*—Each flower lasts 3 days, and a single stem, with its side-branches, will have flowers for a period as great as 2 to 2½ weeks.

*Color.*—This is the reddest iris known to the inventor, its color being approximately Oxblood Red (Plate 1), particularly on the upper surface of the fall petals. But it also has a cast of glittering coppery mahogany tone that gives it a sparkling sheen without making it appear brown-red as many other red varieties do. The three style arms (center of flower) are a shade of orange yellow, approximately Orange Chrome (Plate II), with the center keel lightly influenced by the red coloring of the flower. The beard and standards are bronzy orange, approximately Xanthine Orange (Plate II).

*Fragrance.*—Mild.

*Form of petals.*—Upper petals or standards are broadly arching; lower petals or falls are of modified flare form.

*Size of petals.*—Both types of petals measure approximately 3½ inches from claw to tip.

Reproductive organs:

*Pistil.*—Style arms, three; orange yellow. Center keel slightly red.

*Stamens.*—Filaments, three; measure approximately 1⅞ inches long. Anther approximately ¾ inch long; light yellow.

*Pollen.*—Creamy white; highly fertile.

*Comparison*

The two varieties most like my new variety are Orelio and Redwyne (both unpatented). The principal differences are as follows:

1. My new variety is a truer red than either Orelio or Redwyne, having less brown in its makeup. It has a uniform coppery-mahogany tone of red, whereas Redwyne has standards of bronzy orange with only its falls red, and Orelio is entirely a brown-red.

2. My new variety has a more spherical form of blossom than either, Orelio being somewhat oblong and Redwyne more pointed.

3. My new variety produces flowers which represent an advance in size over both Orelio and Redwyne.

4. When grown under identical conditions, my variety grows 2 to 4 inches taller than Orelio and Redwyne.

5. My new variety has more-widely-spaced blooms, due to its branching stems, which results in freedom from the bunching typical of Orelio and Redwyne.

6. My new variety differs in aspect or "finish" of the flower, it being plushy or velvety in depth and very shiny, whereas Orelio has a more lacquered appearance and Redwyne, although velvety in the falls, has silky standards.

7. My variety has absolutely no visible venation in the haft adjacent to the beard, whereas such venation is quite marked in the case of Orelio.

Having thus disclosed my invention, I claim:

The new and distinct variety of iris plant, substantially as herein shown and described, characterized particularly by its greater height of plant and size of flower over other known red iris varieties; its greater freedom from disease in this color class; its plentiful stem-branching which results in an unusual number of flowers widely spaced; its medium-green foliage; its ease of propagation; and its large, spherical flowers of velvety aspect, substantial texture, absence of distracting venation, and Oxblood Red color with uniform coppery-mahogany overtones.

No references cited.